United States Patent [19]

Zezza

[11] Patent Number: 5,246,967
[45] Date of Patent: Sep. 21, 1993

[54] USE OF ESTERS OF ACYL L-CARNITINES WITH GAMMA-HYDROXYBUTYRIC ACID FOR PRODUCING PHARMACEUTICAL COMPOSITIONS FOR THE TREATMENT OF HEPATOPATHIES

[75] Inventor: Fabio Zezza, Rome, Italy

[73] Assignee: Sigma-Tau Industrie Farmaceutiche Riunite S.p.A., Rome, Italy

[21] Appl. No.: 883,673

[22] Filed: May 15, 1992

[30] Foreign Application Priority Data

May 15, 1991 [IT] Italy ............................ RM91A000327

[51] Int. Cl.⁵ .................... A01N 37/02; A61K 31/225
[52] U.S. Cl. .................................................. 514/547
[58] Field of Search .......................................... 514/547

[56] References Cited

FOREIGN PATENT DOCUMENTS 0442850  8/1991  European Pat. Off. .

Primary Examiner—Frederick E. Waddell
Assistant Examiner—F. Tsung
Attorney, Agent, or Firm—Oblon, Spivak, McClelland, Maier & Neustadt

[57] ABSTRACT

Esters of acyl L-carnitine with gamma-hydroxybutyric acid, both as pharmacologically acceptable salts of formula (1)

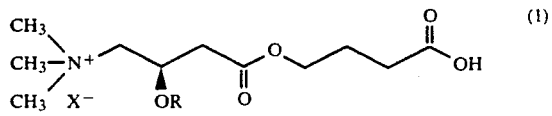

and as inner salts of formula (1')

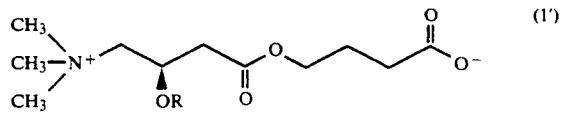

wherein $X^-$ is the anion of a pharmacologically acceptable acid and R is a straight or branched acyl group having from 2 to 5 carbon atoms, are used for producing pharmaceutical compositions effective for treating hepatopathies.

9 Claims, No Drawings

USE OF ESTERS OF ACYL L-CARNITINES WITH GAMMA-HYDROXYBUTYRIC ACID FOR PRODUCING PHARMACEUTICAL COMPOSITIONS FOR THE TREATMENT OF HEPATOPATHIES

The present invention relates to the use of esters of acyl L-carnitines with gamma-hydroxybutyric acid in the form of their pharmacologically acceptable salts of formula (I)

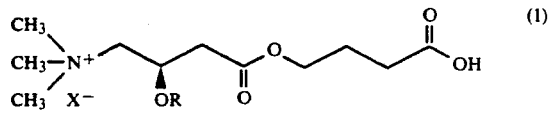

wherein X⁻ is the anion of a pharmacologically acceptable acid e.g. chloride, bromide, orotate, acid aspartate, acid citrate, acid phosphate, acid fumarate, lactate, acid maleate, acid oxalate, acid sulfate and glucosephosphate, or in the form of inner salts of formula (I')

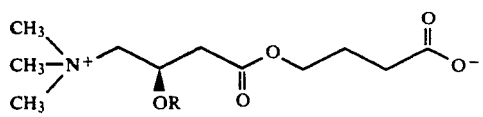

occurs e.g. in Alzheimer's senile dementia and Parkinson's disease) and in the treatment of coma has been also described.

It has now been found that the same compounds of formula (1) and (1') are also potent liver sustaining drugs and can, therefore, be useful for treating liver diseases, e.g. viral hepatitis.

Esters of carnitine with hydroxy-substituted saturated organic acids (e.g. 2-hydroxybutyric, 2-hydroxy-2-methylbutyric and 2-methyl-3-hydroxy propionic acid) are known already; see e.g. U.S. Pat. No. 4,766,222 assigned to SIGMA-TAU Industrie Farmaceutiche Riunite S.p.A. These compounds active on the cardiovascular system are, however, O-esters (i.e. esters on the carnitine hydroxyl group) and endowed with pharmacological properties entirely different from and unrelated to the properties of the esters of the present invention.

Esters on the carnitine carboxyl group are described in Z. Physiol. Chem. 295, 377, 1953 and Z. Physiol. Chem., 346, 314, 1966. These are, however, esters of carnitine with aliphatic alcohols, such as methanol, ethanol and butanol, or with aromatic alcohols such as benzyl alcohol, not with hydroxy-acids.

The examples that follow show the preparation of the esters of acyl L-carnitine with gamma-hydroxybutyric acid via the synthesis scheme wich is illustrated hereinbelow.

Synthesis scheme of the esters of acyl L-carnitine with gamma-hydroxy butyric acid

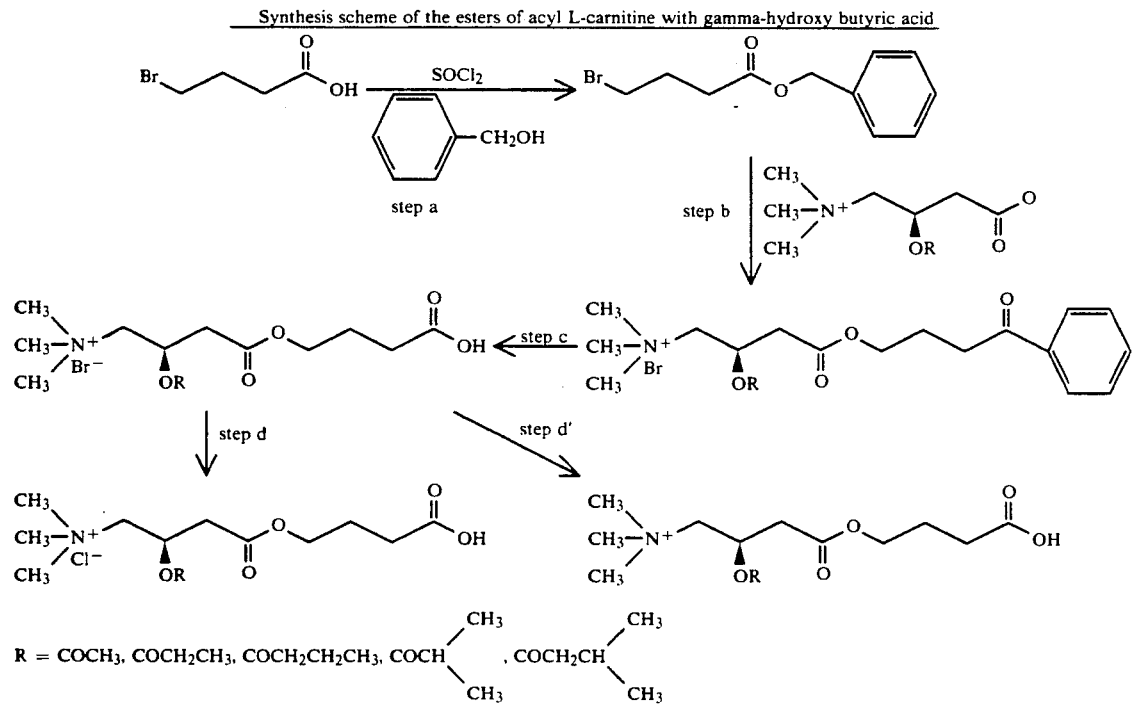

wherein R is a straight or branched acyl group having from 2 to 5 carbon atoms, such as for instance acetyl, propionyl, n-butyryl, isobutyryl and isovaleryl for producing orally or parenterally administrable pharmaceutical compositions for treating hepatopathies.

The esters of acyl L-carnitines with gamma-hydroxybutyric acid of formula (I) and (I') have been already disclosed and claimed in EP patent publication 0442850 A1. In this EP patent publication the utility of these compounds in inhibiting neuronal degeneration (as it

EXAMPLE 1

Preparation of the ester of acetyl L-carnitine with gamma-hydroxybutyric acid (ST 793)

Step A: Preparation of the benzyl ester of gamma-bromobutyric acid

Gamma-bromobutyric acid (3.3 g; 0.02 moles) was suspended in benzyl alcohol (15 ml). The suspension was cooled to 0° C. and thionyl chloride (8 ml; 0.01 moles) was slowly added dropwise thereto. The reaction mixture was kept at room temperature for 16 hours and then concentrated under vacuum to remove thionyl chloride and distilled to remove benzyl alcohol. The distillation residue was purified via chromatography on silica gel, with hexane-AcOEt (98:2) as eluant. TLC hexane $R_F=0.2$ NMR $CDCl_3$ δ7.2(5H,s,aromatic);5.0(2H,s,$CH_2$-benzyl) 3.3(2H,t,$CH_2COO$);2.6-2.0(4H,m,$BrCH_2CH_2$)

Step B: Preparation of the ester of acetyl L-carnitine with benzyl gamma-bromobutyrate Acetyl L-carnitine inner salt (1.62 g; 0.008 moles) was suspended in 12 ml anhydrous dimethyl formamide. To the suspension, gamma-bromobutyric acid benzyl ester (2.05 g; 0.008 moles) was added.

The reaction mixture was kept under stirring at room temperature for 24 hours in a nitrogen atmosphere. Ethyl ether was then added until complete precipitation of the reaction product. The product was isolated by filtration. 3.43 g of the title product were obtained.

TLC $CHCl_3$ 4.2-$H_2O$ 1.1-Isopr OH 0.7-$CH_3COOH$ 1.1 MetOH 2.8 $R_F=0.8$

HPLC
Column μBondapack C18
Eluant $KH_2PO_4$ 0.005M—$CH_3CN$ 70-30
Flow rate 1 ml/min
$R_t$ 12.9
NMR $D_2O$ δ7.4(5H,s,aromatic);5.6(1H,m,

5.2(2H,s,$CH_2$-benzyl); 4.4-4.0(4H,m,$N^+CH_2$, $OCH_2$);3.5(9H,s($CH_3)_3N^+$);3.2(2H,d,CH—$\underline{CH}_2COO$);2.3(2H,m,$CH_2CH_2COO$); $\overline{2.0(5H,m,^+,CH_2CH_2CH_2; COCH_3)}$ Step C: Preparation of the ester of acetyl L-carnitine bromide with gamma-hydroxybutyric acid The product of step B (1 g) was dissolved in 20 ml absolute ethanol. The resulting solution was hydrogenated in the presence of 100 mg 10% Pd/C under 3 atmospheres of hydrogen for 30 minutes. The mixture was filtered and concentrated under vacuum. 0.075 g of the title product were obtained. Yield 98%. TLC as in step B $R_F=0.7$.

Step D: Preparation of the ester of acetyl L-carnitine with gamma-hydroxybutyric acid inner salt (I')

The product of step C (1 g) was eluted through 30 ml strongly basic resin (AMBERLITE IRA 402) activated in the $HCO_3-$ form. The eluate was lyophilized.

An extremely hygroscopic solid product was obtained.

NMR($D_2O$):δ5.6(1H,m,

4.2(2H,t,—$CH_2O$);3.7(2H,d,—$N^+CH_2-$); 3.2(9H,s,$(CH_3)_3N^+$);2.8(2H,d,$CH_2COO$);2.3-2.0(5H,m+s,$CH_2COO$; $COCH_3$);1.8(2H,m,$CH_2$—$\underline{CH}_2COOH$)

$[\alpha]_D^{25}=-18.0$ (C=1,$H_2O$)
HPLC

Column spherisorb -SCX 5M
Eluant $KH_2PO_4$ 0.005M —$CH_3CN$(35-65); pH=4.2
Flow rate 1 ml/min
Detector UV 205 nm
$R_t=8.83$
TLC as in step B $R_F=0.5$

EXAMPLE 2

Preparation of the ester of isovaleryl L-carnitine with gamma-hydroxybutyric acid (ST 794).

Step A: as in Example 1

Step B: Preparation of the ester of isovaleryl L-carnitine with gamma-hydroxybutyric acid benzyl ester Isovaleryl L-carnitine inner salt (2 g; 0.01 moles) was suspended in 15 ml dimethyl formamide and to the resulting mixture 4-bromo butyric acid benzyl ester (2.65 g; 0.01 moles) was added. The reaction mixture was kept under stirring at room temperature in a nitrogen atmosphere overnight. Ethyl ether was then added to the mixture until complete precipitation. 2 g of the compound were obtained.

TLC as in step B of Example 1 $R_F=0.7$
Column μBondapack $C_{18}$
Eluant $KH_2PO_4$ 0.05M —$CH_3CN$ 50-50
Flow rate 1 ml/min
$R_t=9.27$
NMR $D_2O$ δ7.2(5H,s,aromatic);5.6(1H,m,

5.0(2H,s,$CH_2$-Ar) (2H,t,$COOCH_2$);3.9-3.6(2H,m,$N+CH_2$);3.2(9H,s,$(CH_3)_3N+$); 2.8(2H,m,$CHCH_2COO$);2.4(2H,t,$CH_2CH_2COO$);2.2(2$\overline{H}$,d,$OCOCH_2$); 2.0-1.8(3$\overline{H}$,m,

—$CH_2\underline{CH}_2CH_2COO$);0.9(6H,d,

Step C: Preparation of the ester of isovalery L-carnitine bromide with gamma-hydroxybutyric acid The product of step B (1 g) was dissolved in 20 cc $H_2O$ and hydrogenated in the presence of 10% Pd/C at a pressure of 3 atmospheres for 30 minutes. The mixture was filtered and concentrated under vacuum. 0.78 g were obtained.

Yield 98%
HPLC
Column spherisorb-SCX
Eluant $CH_3CN$-$KH_2PO_4$ 0.5M 65-35
Flow rate 1 ml/min
$R_t=6.46$
NMR $D_2O$ δ5.7(1H,m,

4.2(2H,t,—COOCH₂);4.0-3.7(2H,m,N⁺CH₂); 3.2(9H,s,(CH₃)₃N⁺);2.9(2H,d,CHCH₂—COO);2.4(4H,-m,OCOCH₂+CH₂COOH);2.0(3H,m,

+CH₂CH₂CH₂);0.9(6H,d,

$[\alpha]_D^{25} = -15.1$ (C=1% H₂O)

EXAMPLE 3

Preparation of the ester of isobutyl L-carnitine chloride with gamma-hydroxybutyric acid (ST 878).

Step A: same as in Example 1

Step B: preparation of the ester of isobutyryl L-carnitine bromide with gamma-hydroxybutyric acid benzyl ester This step was carried out as step B in Example 1, except that isobutyryl L-carnitine inner salt was substituted for acetyl L-carnitine inner salt.

$[\alpha]_D^{25} = -11.7$ (C=1% H₂O)
HPLC
Column μBondapak C₁₈ 3.9 mm ID
mobile phase KH₂PO₄ 0.05M —CH₃CN (70-30)
Flow rate 1.4 ml/min
Rt=20.54 min
NMRD2O δ7.3(5H,s,benzyl);5.6(1H,m,

5.1(2H,s,CH2-benzyl); 4.2-3.8(4H,m,COOCH₂;N⁺CH₂—);3.2(9H,s,(CH₃)₃N⁺);2.8(2H,CH—CH-₂COO);2.5-2.2(3H,m,CH₂CH₂COOH,OCOCH); 1.8(2H,q,CH₂CH₂COO);1.1(6H,d,

Yield: 95%

Step C: Preparation of the ester of isobutyryl L-carnitine chloride with gamma-hydroxybutyric acid The product of step B was hydrogenated as described in step C of Example 1. The product thus obtained was converted directly into chloride with AMBERLITE IRA 402 resin activated in Cl⁻ form. The eluate was lyophilized thus giving the title product.

$[\alpha]_D^{25} = -29.7$ (C=1% H₂O)
HPLC
Column μBondapak NH2 10μ
mobile phase KH₂PO₄ 0.05M —CH₃CN (35-65)
Flow rate 1 ml/min
Rt=5.26 min
NMRD2O δ5.6(1H,m,

4.2(2H,t,COOCH₂);3.8(2H,m,N⁺CH2)
3.2(9H,s,(CH₃)₃N⁺2.9(2H,d, CH-CH₂COO);2.7-2.2(3H,m,

CH₂COOH);1.8(2H,q,CH₂CH₂COOH);1.0(6H,d,

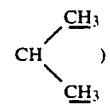

TLC silica gel
CHCl₃-4-IsoprOH 0.7-MetOH-3-CH₃COOH-1-H₂O
1
Rf=0.65
E.A. C₁₅H₂₈ClNO₆

|  | C % | H % | N % | Cl % |  |
|---|---|---|---|---|---|
| calc. | 50.91 | 7.97 | 3.95 | 10.02 | KF 2% |
| calc. with 2% H₂O | 49.89 | 8.04 | 3.87 | 9.81 |  |
| found | 50.00 | 8.43 | 4.07 | 9.98 |  |

Yield: 98%

EXAMPLE 4

Preparation of the ester of propionyl L-carnitine bromide with gamma-hydroxybutyric acid benzyl ester.

Step A: as in Example 1

Step B: preparation of the ester of propionyl L-carnitine bromide with gamma-hydroxybutyric acid (ST 880).

This step was carried out as step B in Example 1, except that propionyl L-carnitine inner salt was substituted for acetyl L-carnitine inner salt.

$[\alpha]_D^{25} = -12.8$ (C=1% H₂O)
HPLC
Column μBondapak C₁₈ 3.9 mm ID
Mobile phase NaClO₄ 0.05M —CH₃CN (70-30)
Flow rate 2 ml/min
Rt=20.9 min
NMRD2O δ7.4(5H,s,benzyl);5.8(1H,m

5.1(2H,s,CH₂-benzyl); 4.2(2H,t,O-CH₂CH₂);3.8(2H,m,N⁺—CH₂);3.3(9H,s,(CH₃)₃N⁺); 2.8(2H,d,CH—CH₂COO);2.6-2.3(4H,m, CH₂CH₃;CH₂—CH₂—COO); 2.0(2H,q,CH₂—CH₂CH₂);1.1(3H,t,CH₂—CH₃)
Yield: 70%

Step C: preparation of the ester of propionyl L-carnitine chloride with gamma-hydroxybutyric acid The product of step B was hydrogenated as described in step C of Example 1.

The product thus obtained was converted directly into chloride using an AMBERLITE IRA 402 resin activated in Cl⁻ form. The eluate ws lyophilized thus giving the title product.

$[\alpha]_D^{25} = -22.2$ (C=1% H$_2$O)

HPLC

Column μBondapak -NH$_2$ (10 μ)
mobile phase KH$_2$PO$_4$ 0.05M—CH$_3$CN (35-65)
Flow rate 1 ml/min
Rt=6.16 min
NMRD$_2$O 5.7(1H,m,

4.2(2H,t,COOCH$_2$);3.9-3.7(2H,m,N+CH$_2$)
3.2(9H,s,(CH$_3$)$_3$N+);2.8(2H,d,CHCH$_2$COO)2-.7-2.3(4H,m,CH$_2$CH$_3$;
COOCH$_2$CH$_2$);2.0(2H,m,CH$_2$CH$_2$COOH);1.1(3H,t,CH$_2$CH$_3$)

TLC SILICA GEL
CHCl$_3$-4-Isopr OH-0.7-MetOH-3-CH$_3$COOH-1-H$_2$O 1
Rf=0.55
Yield: 98%

PHARMACOLOGICAL STUDIES

Pharmacological studies were conducted to assess the liver protecting activity of the compounds of this invention in laboratory animals in which liver damage had been induced by D-galactosamine intoxication.

Liver protecting activity was also assessed with a study of hepatic proteolysis in perfused rat liver model.

(1) D-galactosamine-induced intoxication

As known, D-galactosamine administered to laboratory animals produces pathological alterations similar to human viral hepatitis.

Male Wistar rats, weighing 200-250 grams after having been caged on a 12-hour light and dark cycle for about one week were used. Food and water were freely available. The rats were kept fasting for 18 hours before the test started.

Following the conditioning, the animals were divided in groups with 15 animals in each group, taking care to collect animals having substantially identical body weights in the same group In order to induce liver damage, 500 mg/kg body weight of D-galactosamine dissolved in 0.9% saline (pH=7.4) were administered i.p. in 5 mL/kg body weight.

1 hour, 8 hours and 24 hours following hepatotoxicant administration, the animals were orally administered 0.35 mM/kg ST 794 dissolved in water.

32 hours following hepatotoxicant administration, the animals were sacrificed by decapitation and the blood collected in 100 cc plastic test tubes.

Blood was centrifuged (3,000 rpm) and on the serum thus obtained transaminases (SGOT, SGPT), glycaemia, bilirubin and urea were assayed.

These parameters are suitable for assessing the intoxication level induced in laboratory animals since a typical symptom of liver damage is the appearance of increased enzyme activity in serum.

The decrease of transaminases (SGOT, SGPT) was comprised between 30 and 60%, and bilirubin decrease exceeded 60%.

The data are statistically significant (p<5). Glycaemia and urea were not modified.

(2) Perfused rat liver

The perfused liver test was carried out following the method by Mortimore and Poso, Multiphasic control of hepatic protein degradation by regulatory amino acids, *Journal of Biological Chemistry* 262: 16322-16327 (1987).

Male Wistar rats weighing 130-140 grams fed on free diet were used. The liver perfusion apparatus was substantially identical to that described by Seglen, Preparation of isolated rat liver cells. *Methods in cell Biology* vol. 13, Ac Press. N.Y. pp. 29-83 (1976), and consisted of a hydraulic recirculating system for adjusting the temperature of the whole perfusion apparatus. Recirculation was assured by a hydraulic pump and a water-bath; a peristaltic pump was used for carrying out the perfusion.

A source of oxygen/carbon dioxide [O$_2$/CO$_2$, 95/5%(v/v)] assured oxygenation of perfusion buffers. The samples were assayed via HPLC.

The animals were anaesthetized by i.p. injection of Ketamine or Ketalar (16 mg/100 g) and then heparinized (1000 U) just before portal vein cannulation.

The perfusion medium consisted of Krebs-Ringer bicarbonate buffer and 4.0% (p/v) of bovine plasma albumine (Fraction V, Sigma Chemical), balanced for at least one hour before perfusion (pH=7.4) by gassing it with O$_2$/CO$_2$ 95/5% (v/v).

Albumin was added to the buffer just before its use and following dialysis against 2-4 liters 0.9% saline and filtration through a 0.45 μm MILLIPORE filter.

The composition of Krebs-Ringer buffer was as follows:118.46 mM NaCl; 4.74 mM KCl; 1.18 mM KH$_2$PO$_4$; 1.18 mM MgSO$_4$; 1.048 g (24 mM) NaHCO$_3$; 10 mM glucose (only for non recirculating perfusion); pH=7.4.

The buffer was gassed with O$_2$/CO$_2$ 95/5% (v/v) for one hour. To the perfusion medium 0.22 mM, 0.44 mM and 0.88 mM ST 794, respectively, were added. The whole perfusion apparatus was kept at a steady temperature of 37° C.

At the end of 40-minute non recirculating perfusion (20 mL/min), a second, recirculating step was carried out wherein 50/60 mL of glucose-free buffer were perfused for 15-20 minutes following a 40-second wash-out period.

At the beginning of this second step, cycloheximide was added to stop hepatic proteosynthesis and assess net proteolysis.

10-15 minutes following the beginning of recirculating perfusion, 1-ml perfusate samples were drawn and stored at −80° C.

Valine concentration (expressed as nmoles valine/mL perfusate/ gram fresh liver) was taken as parameter for evaluation of liver proteolysis.

A pronounced decrease of hepatic proteolysis was shown at concentrations of 0.88 and 0.44 mM ST 794. In fact, valine release decreased by 35% at 0.88 mM and by 21% at 0.44 mM concentration.

The compounds of the present invention are orally or parenterally administered, in any of the usual pharmaceutical forms which are prepared by conventional procedures well-known to those persons skilled in pharmaceutical technology. These forms include solid and liquid oral unit dosage forms such as tablets, capsules, solutions, syrups and the like as well as injectable forms, such as sterile solutions for ampoules and phials.

For these pharmaceutical forms the usual solvents, diluents and excipients are used. Optionally, sweetening, flavouring and preservative agents can also be present. Non-limiting examples of such agents are sodium carboxymethylcellulose, polysorbate, mannitol, sorbitol, starch, avicel, talcum and other agents which will be apparent to those skilled in the pharmaceutical technology.

The dose which is administered will be determined by the attending physician having regard to the age, weight and general conditions of the patient, utilizing sound professional judgement. Although effective results can be noticed at doses as low as 5 to 8 mg/kg of body weight daily, a dose of from about 10 to about 50 mg/kg of body weight is preferred. Whenever necessary, larger doses can be safely administered in view of the low toxicity of the compounds of this invention.

As non-limiting examples and depending on the specific pharmaceutical form of administration, the following dosages can be indicated:

for the phials: from 50 to 500 mg
for the capsules: from 20 to 50 mg
for the tablets: from 20 to 500 mg
for the oral solution: from 20 to 50 mg

I claim:

1. A process for treating a hepatopathy in a patient in need of such treatment which comprises orally or parenterally administering to the patient a therapeutically effective amount of an ester of acyl L-carnitine with gamma-hydroxybutyric acid.

2. A process according to claim 1, wherein the hepatopathy is viral hepatitis.

3. A process according to claim 2, wherein the ester is in the form of a pharmacologically acceptable salt of formula (1)

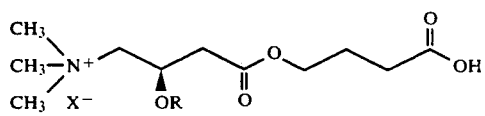

wherein $X^-$ is the anion of a pharmacologically acceptable acid and R is a straight or branched acyl group having for 2 to 5 carbon atoms.

4. A process according to claim 2, wherein the ester is in the form of an inner salt (1')

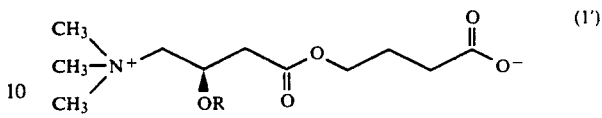

wherein R is a straight or branched acyl group having from 2 to 5 carbon atoms.

5. A process according to claim 1, wherein the ester is in the form of a pharmacologically acceptable salt of formula (1)

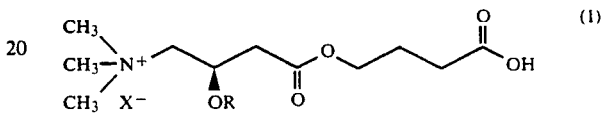

wherein $X^-$ is the anion of a pharmacologically acceptable acid and R is a straight or branched acyl group having from 2 to 5 carbon atoms.

6. A process according to claim 1, wherein the ester is in the form of an inner salt (1')

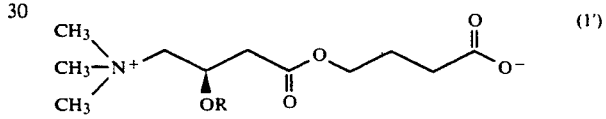

wherein R is a straight or branched acyl group having from 2 to 5 carbon atoms.

7. A process according to claim 6, wherein the ester is an acetyl, propionyl, n-butyryl, isobutyryl or isovaleryl L-carnitine gamma-hydroxybutyrate.

8. A process according to claim 5, wherein the ester is an acetyl, propionyl, n-butyryl, isobutyryl or isovaleryl L-carnitine gamma-hydroxybutyrate.

9. A process according to claim 5, wherein $X^-$ is an anion selected from the group consisting of chloride, bromide, orotate, acid aspartate, acid citrate, acid phosphate, acid fumarate, lactate, acid maleate, acid oxalate, acid sulfate and glucosephosphate.

* * * * *